(12) United States Patent
Louw et al.

(10) Patent No.: US 6,178,968 B1
(45) Date of Patent: Jan. 30, 2001

(54) METHOD OF ENDOSCOPICALLY VISUALIZED OCCLUSION OF THE SIDE BRANCHES OF AN ANATOMICAL PASSAGEWAY

(75) Inventors: Frank Louw, Carlsbad; Stephen A. Sosnowski, Oceanside, both of CA (US); David Rosenthal, Marietta, GA (US)

(73) Assignee: Edwards Lifesciences Corp., Irvine, CA (US)

( * ) Notice: Under 35 U.S.C. 154(b), the term of this patent shall be extended for 0 days.

(21) Appl. No.: 09/306,863

(22) Filed: May 7, 1999

Related U.S. Application Data (63) Continuation of application No. 08/910,944, filed on Aug. 8, 1997, now Pat. No. 5,947,994, which is a continuation of application No. 08/486,038, filed on Jun. 7, 1995, now Pat. No. 5,707,389.

(51) Int. Cl.[7] .................. A61M 29/00; A61M 25/00; A61B 1/00

(52) U.S. Cl. .................. 128/898; 600/106; 600/170; 606/200; 604/523

(58) Field of Search .......... 606/200; 600/106, 600/170; 128/898; 604/523

(56) References Cited

U.S. PATENT DOCUMENTS

| | | |
|---|---|---|
| 1,303,135 | 5/1919 | Wappler . |
| 1,928,992 | 10/1933 | Clark et al. ............... 137/90 |
| 2,143,960 | 1/1939 | Stalter et al. ............ 138/49 |
| 4,175,545 | 11/1979 | Termanini .............. 128/666 |
| 4,353,358 | 10/1982 | Emerson ................. 128/4 |
| 4,420,016 | 12/1983 | Nichols ................. 138/103 |
| 4,461,282 | 7/1984 | Ouchi et al. ............. 128/4 |
| 4,529,009 | 7/1985 | Horner et al. ......... 138/111 |
| 4,576,145 | 3/1986 | Tsuno et al. ............ 128/6 |
| 4,616,631 | 10/1986 | Takahashi .............. 128/6 |
| 4,617,914 | 10/1986 | Ueda ..................... 128/4 |
| 4,619,247 | 10/1986 | Inoue et al. ............. 128/6 |
| 4,686,963 | 8/1987 | Cohen et al. ............. 128/4 |
| 4,706,656 | 11/1987 | Kuboto .................. 128/6 |
| 4,736,733 | 4/1988 | Adair .................... 128/6 |
| 4,757,819 | 7/1988 | Yokoi et al. ........... 128/660 |
| 4,844,062 | 7/1989 | Wells .................. 128/303 |
| 4,881,524 | 11/1989 | Boebel et al. ........... 128/6 |

(List continued on next page.)

FOREIGN PATENT DOCUMENTS

| | | |
|---|---|---|
| 3916288 | 11/1989 | (DE) . |
| 0306723 | 3/1989 | (EP) . |
| 0335523 | 10/1989 | (EP) . |
| 0369936 | 5/1990 | (EP) . |
| 1099949 | 6/1984 | (SU) . |
| 85/02101 | 5/1985 | (WO) . |
| 92/01414 | 2/1992 | (WO) . |

*Primary Examiner*—V. Millin
*Assistant Examiner*—Choon P. Koh
(74) *Attorney, Agent, or Firm*—Peter Jon Gluck; Guy Cumberbatch; Bruce M. Canter (57) ABSTRACT

Methods for utilizing a device for blocking (e.g., embolizing) the side branches of an anatomical passageway under endoscopic guidance. The device comprises an elongate catheter body having a side branch blocking apparatus, such as an embolization catheter, disposed therein and further incorporating an endoscope (e.g., an angioscope). The incorporated endoscope is useable to a) visually locate side branches which emanate from the anatomical passageway and b) visually observe the operation of the side branch blocking apparatus. Disclosed are methods for performing in situ embolization of the side branches of a vein, under angioscopic visualization. The endoscopic component of the device may also be utilized to visually observe the use and/or effect of one or more separate device, such as valvulotome(s) used for cutting venous valves located within the lumen of a vein.

16 Claims, 5 Drawing Sheets

U.S. PATENT DOCUMENTS

| | | | |
|---|---|---|---|
| 4,906,496 | 3/1990 | Hosono et al. | 428/36.9 |
| 4,919,112 | 4/1990 | Siegmund | 128/4 |
| 4,942,866 | 7/1990 | Usami | 128/4 |
| 4,973,321 | 11/1990 | Michelson | 604/280 |
| 5,114,402 | 5/1992 | McCoy | 604/95 |
| 5,156,141 | 10/1992 | Krebs et al. | 128/4 |
| 5,156,142 | 10/1992 | Anapliotis | 128/6 |
| 5,156,590 | 10/1992 | Vilmar | 604/4 |
| 5,158,086 | 10/1992 | Brown et al. | 128/662.03 |
| 5,201,756 | 4/1993 | Horzewski et al. | 606/198 |
| 5,213,093 | 5/1993 | Swindle | 128/4 |
| 5,257,618 | 11/1993 | Kondo | 128/4 |

METHOD OF ENDOSCOPICALLY VISUALIZED OCCLUSION OF THE SIDE BRANCHES OF AN ANATOMICAL PASSAGEWAY

RELATED APPLICATIONS

This is a continuation of application Ser. No. 08/910,944, filed Aug. 8, 1997, now U.S. Pat. No. 5,947,994 which is a continuation of application Ser. No. 08/486,038, filed on Jun. 7, 1995, now U.S. Pat. No. 5,707,389.

BACKGROUND OF THE INVENTION

1. The Field of the Invention

This invention relates generally to medical devices and methods, and more particularly to a method for performing endoluminal embolization of the side branches of a tubular anatomical passageway such as a blood vessel.

2. Description of the Related Art

In clinical medicine, it is sometimes desirable to selectively block certain blood vessels or anatomical passageways of the body. For example, the selective blockage of blood vessels may be utilized as a means of a) creating localized hemostasis to treat or prevent hemorrhage; b) blocking blood flow through an aneurysmic region of an artery; c) blocking the blood supply to a tumor; and d) closing off the side branches of a blood vessel segment which is to be subsequently utilized as a graft for replacing or bypassing an occluded artery.

One particular type of surgical procedure wherein a segment of vein is utilized to bypass a blocked artery is known as an in situ vein bypass procedure. Such in situ vein bypass procedure are often used as a means of treating patients in whom a leg artery (e.g., the femoral artery or the popliteal artery) has become occluded due to atherosclerotic disease. In these procedures, a vein which runs generally parallel to the occluded artery is prepared by a) transecting the vein at locations above and below the arterial blockage, b) inserting a valvulotome device into the lumen of the vein segment to disrupt or lyse all venous valves located therewithin, and c) blocking all side branches of the vein segment. Thereafter, the ends of the vein segment are anastomosed to the blocked artery, at locations above and below the blockage, thereby forming a bypass conduit around the arterial blockage.

In the past, the methods used for blocking the side branches of the vein segment for later use in an in situ bypass procedure required either a) surgical exposure and dissection of an entire vein segment to locate and ligate all of the side branches which emanate therefrom, or b) the use of angiographic radiological techniques to locate the vein side branches so that small individual incisions could be made to access and ligate each side branch. These prior art side branch blocking procedures were, however, associated with numerous problems. For example, the open surgical exposure and dissection of the entire vein segment resulted in a sizable incision, with accompanying potential for wound infection and post operative discomfort. Alternatively, the use of angiographic radiological techniques for location of the side branches resulted in substantial radiation exposure of the patient, and required the injection of contrast media into the vein to facilitate fluoroscopic visualization of the side branches.

More recently, efforts have been undertaken to develop simplified endovascular techniques whereby the side branches of the vein segment may be directly visualized by way of an angioscope inserted into the vein and an endovascular embolization catheter may be utilized to perform endoluminal embolization of the side branches, without requiring surgical exposure of the side branches or the injection of radiographic contrast fluid.

The use of these endovascular embolization catheters under direct angioscopic visualization has typically required that a separate angioscope be utilized for the purpose of a) visually locating the venous side branches and b) visually observing and guiding the endovascular side branch embolization procedure.

The manipulation and use of an angioscope which is separate from the embolization catheter has proven to be problematic. In particular, it is difficult to maintain proper positioning of the angioscope so as to a) carefully locate all venous side branches within the vein segment and b) properly visualize and observe the endovascular side branch embolization procedure. Also, these procedures typically require that the separate angioscope be inserted in a direction which is retrograde to, or opposite, the direction in which the embolization catheter is inserted. This results in a less than optimal vantage point for visualizing the side branches because the normal anatomical angle of the side branches is obtuse to the direction in which the embolization catheter is inserted, thereby resulting in the luminal openings into the side branches being angled away from the vantage point provided by an angioscope which has been inserted in the opposite direction.

Thus, there exists a need in the art for the development of an improved endovascular side branch blocking device (e.g., an embolization catheter) which incorporates an integrated angioscope which is usable to a) clearly locate venous side branches from a vantage point located on the device, as the device is advanced through the lumen of the vein segment and b) visually observe and verify the blocking of each side branch by use of the side branch blocking device (e.g., embolization catheter).

SUMMARY OF THE INVENTION

The present invention provides a method and device for performing endoluminal embolization of the side branches of an anatomical passageway (e.g., a blood vessel) under endoscopic (e.g., angioscopic) visualization. The device of the present invention comprises a) an elongate, flexible catheter body having first and second lumens extending longitudinally therethrough; b) a side opening formed in the catheter body near the distal end thereof, said side opening being communicative with the second lumen of the catheter body; c) an embolization device disposed within the second lumen of the catheter body and operative to pass at least one embolization member out of the side opening of the catheter body; and d) an endoscope (e.g., an angioscope) disposed within the first lumen of the catheter body, and moveable back and forth between i) a distally advanced position whereat the endoscope is positioned to provide viewing of an area ahead of the distal end of the catheter body; and, ii) a proximally retracted position whereat the endoscope is positioned to provide viewing of the side opening of the catheter body (without obstructing passage of an embolization member out of the side opening).

In accordance with the method of the present invention, the device of the forgoing character may be operated such that the endoscope (e.g., angioscope) of the device is initially positioned in its distally advanced position to permit viewing and location of side branches that emanate from an anatomical passageway as the catheter body is being advanced, distal end first, through the anatomical passageway; and, thereafter the endoscope may be subsequently retracted to its proximally retracted position to permit viewing of the passage of an embolization member out of the side opening and into a side branch of the anatomical passageway.

Further objects and advantages of the invention will become apparent to those skilled in the art upon reading and understanding of the following detailed description and the accompanying drawings.

DESCRIPTION OF THE PREFERRED EMBODIMENTS

The following detailed description and the accompanying drawings are provided for purposes of describing and illustrating presently preferred embodiments of the invention only, and are not intended to limit the scope of the invention in any way.

i. The Preferred Device

With reference to the accompanying figures, a preferred device 10 of the present invention comprises an elongate, flexible catheter body 12 having a proximal end PE and a distal end DE. The catheter body 12 comprises a dual lumen tube having a first lumen 14 and a second lumen 16 extending longitudinally therethrough. A distal tip member 18 is attached to the distal end of the dual-lumen tube, as shown. The distal tip member 18 comprises a rigid, generally cylindrical member having a distal portion DP of a first diameter and a proximal tubular member 36 of a smaller second diameter. The proximal tubular member 36 of the distal tip member 18 is inserted into and secured to the dual-lumen tube such that the distal tip member 18 forms the distal end of the catheter body 12. The distal tip member 18 includes a first luminal trough 20 which, when properly positioned, is in alignment with the first lumen 14 of the catheter body 12. Also, the distal tip member 18 comprises a second lumenal passageway 22 which, when properly positioned, is in alignment with the second lumen 16 of the catheter body 12. The distal face 24 of the distal tip member 18 is substantially closed, except for a generally U-shaped angioscopic view port 26 formed at the distal end of the first lumenal trough 20. In the preferred embodiment, the generally U-shaped angioscopic view port 26 has a tapered or chamfered edge, as shown.

Figure 3A:
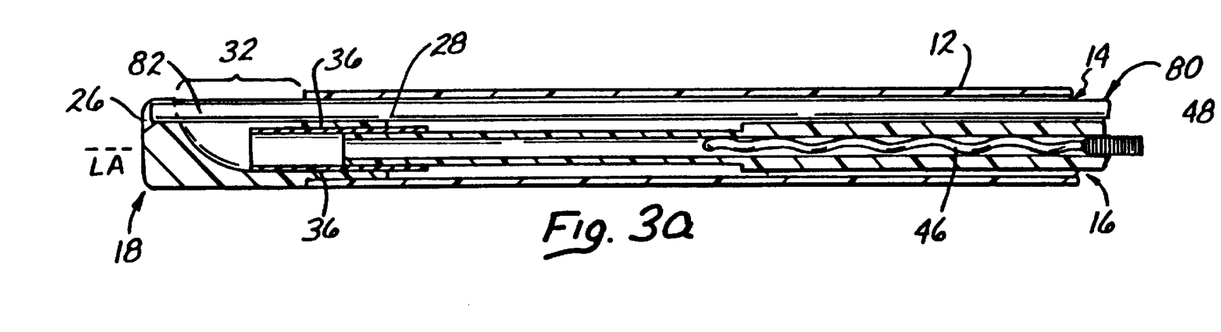
FIG. 3a is a longitudinal sectional view of the distal end of the device of FIG. 1 with the angioscopic component of the device positioned in its distally advanced position.
Figure 3B:
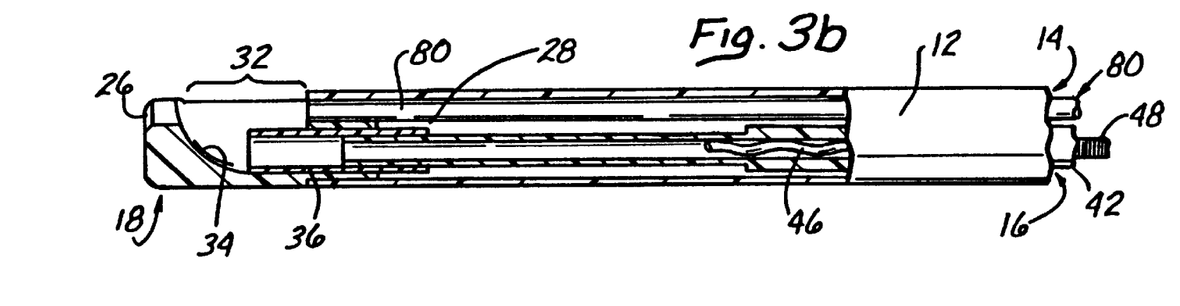
FIG. 3b is a longitudinal sectional view of the distal end of the device of FIG. 1 with the angioscopic component of the device in its proximally retracted position.

With reference to FIG. 3a, a bulkhead 28 exists between the first lumen 14 and the second lumen 16 of the catheter body 12. Such bulkhead 28 terminates a spaced distance proximal to the distal face 24 of the distal tip member 18. A generally U-shaped angioscope supporting ledge 30 is formed immediately proximal to the angioscope view port 26 formed in the distal face 24 of the distal tip member 18. Such angioscope supporting ledge 30 is in alignment with the generally U-shaped floor of the first lumenal trough 20. A side opening 32 exists within the distal tip member 18, proximal to the distal end surface 24 and distal to the distal most extent of the bulkhead 28, as shown in FIG. 3b. A curved or angular deflection surface 34 is formed in the interior of the distal tip member 18, between the distal end of the second luminal passageway 22 and the side opening 32 of the distal tip member 18. In the embodiment shown, the deflection surface 34 is of a radiused or curved configuration. It will be appreciated however, that such deflection surface 34 may be in the form of an angular bend or any other shape which will deflect the advancing distal tip member 18 out of the side opening 32. A rigid sleeve member 36 is fixedly mounted within the proximal portion of the second lumenal passageway of the distal tip member 18, and extends partially into the distal portion DP thereof, as shown. This rigid sleeve member 36 inserts into the second lumen 16 of the catheter body 12, beneath bulkhead 28, and serves as a guide for a distal tubular portion 40 of an embolization device 42 which is disposed within the second lumen 16 of the catheter body 12.

Figure 5:
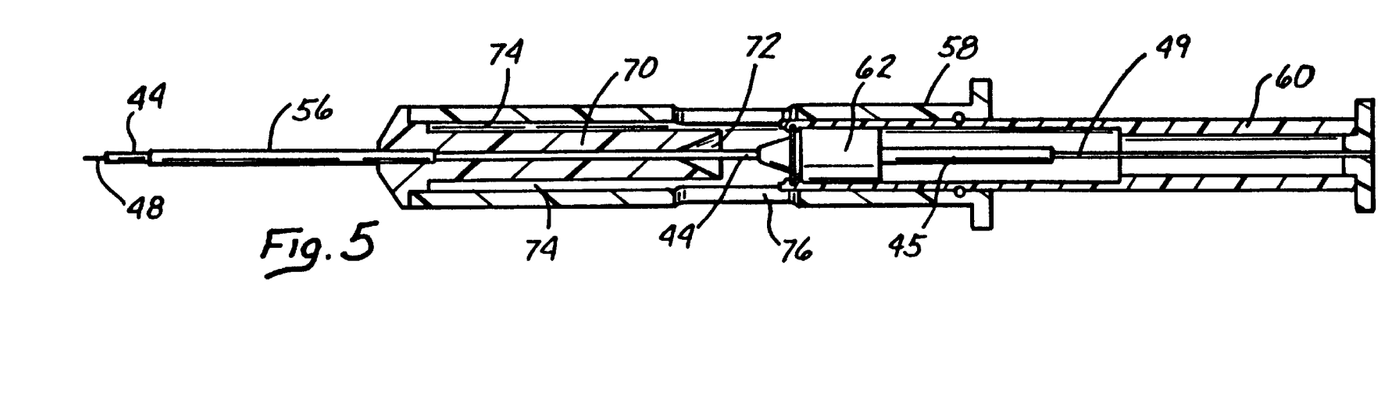
FIG. 5 is a longitudinal sectional view through line 5—5 of FIG. 4.

With reference to FIGS. 3b and 5, the embolization device 42 comprises an elongate pliable embolization catheter body 44 having the distal tubular member 40 extending from the distal end thereof A resilient embolization coil 46 is disposed within the lumen of the embolization catheter body 44 and or distal tubular member 40. Such embolization coil 46 is positioned ahead of a push wire 48, said push wire 48 being disposed within the lumen of the catheter body 44.

Figures 1, 2A:
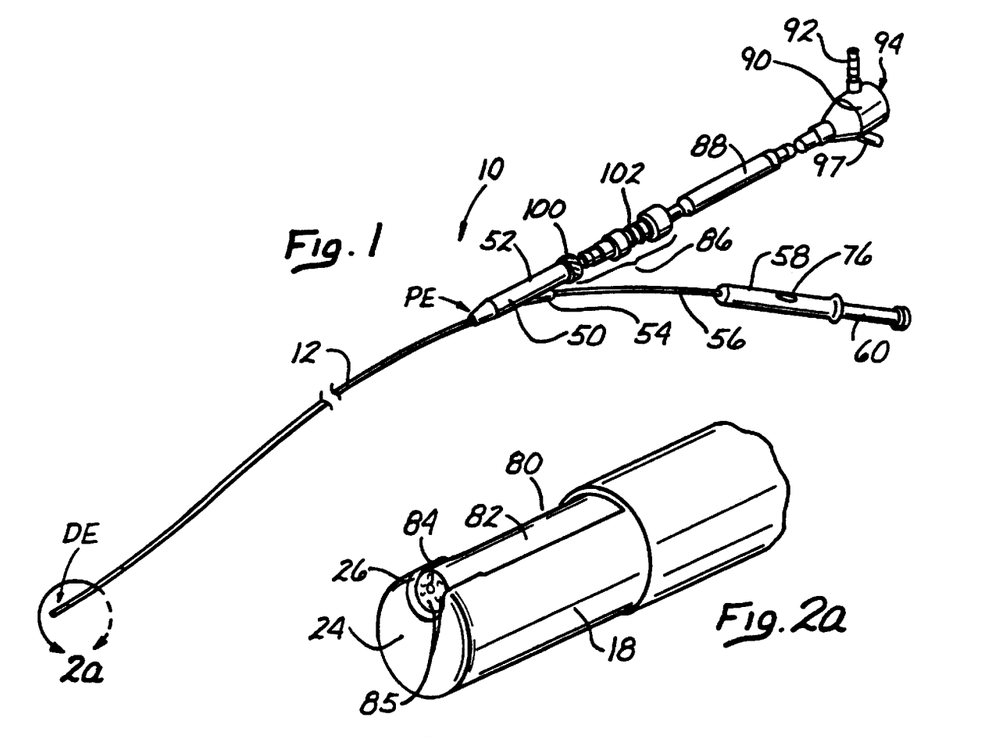
FIG. 1 is perspective view of one embodiment of the device of the present invention.
FIG. 2a is an enlarged perspective view of the distal end of the device of FIG. 1, with the angioscopic component of the device positioned in its distally advanced position.
Figure 4:
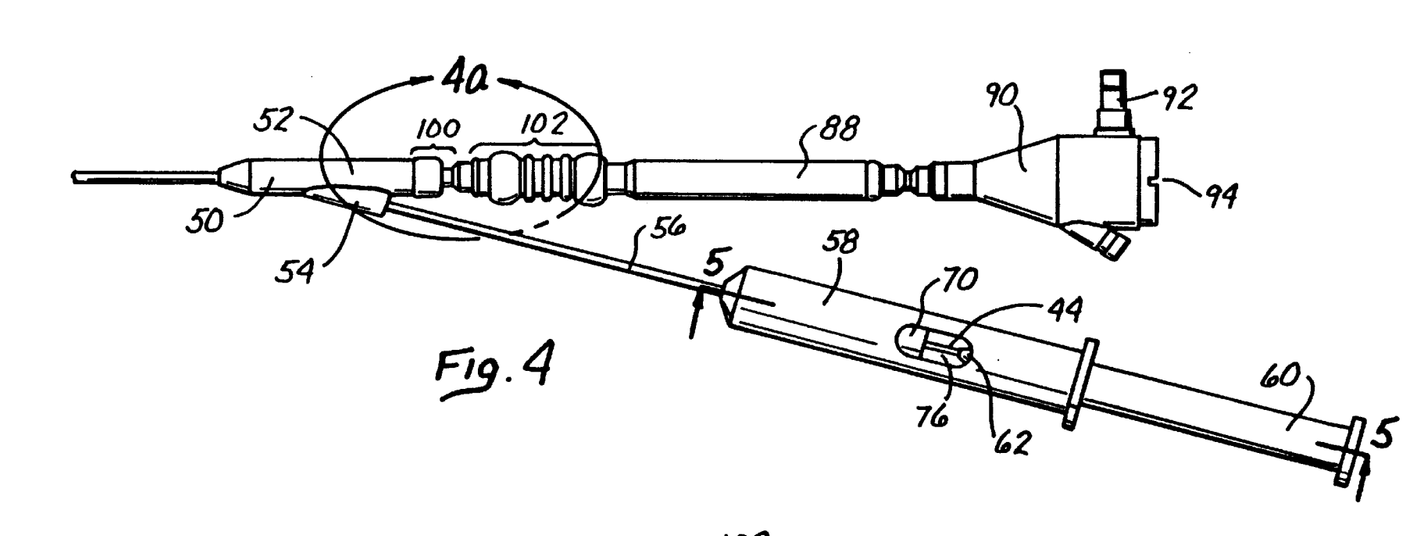
FIG. 4 is an enlarged elevational view of the proximal assembly portion of the device of FIG. 1.
Figure 4A:
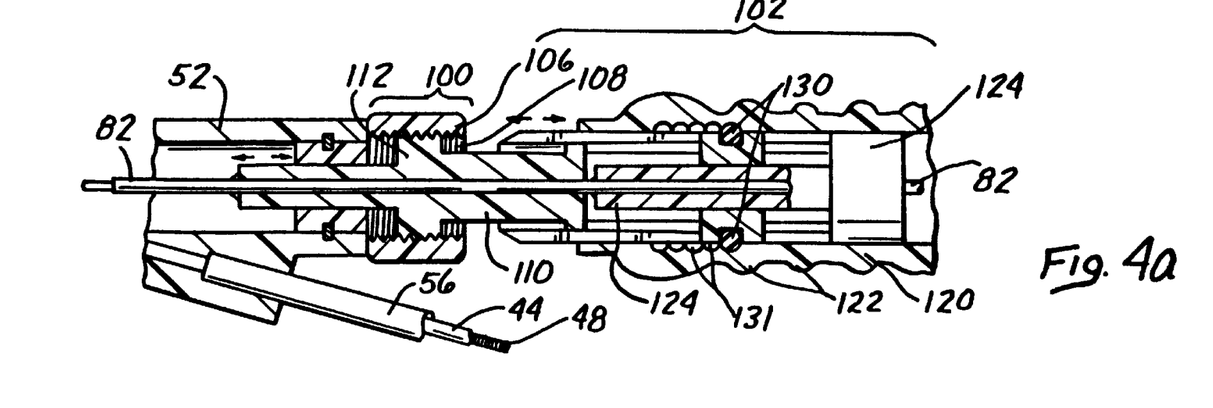
FIG. 4a is an enlarged longitudinal sectional view of segment 4a of FIG. 4.

With reference to FIGS. 1 and 4, proximal Y-connector 50 is positioned on the proximal end of the catheter body 12. The proximal Y-connector 50 comprises a main body portion 52 and a side arm 54. An extension tube 56 and embolization device plunger barrel 58 extend out of the side arm 54 of the proximal Y-connector 50. As seen in FIGS. 4a and 5, the catheter body 44 and push wire 48 extend through the side arm 54 of the Y-connector 50, through the tubular extension 56 and into the interior of a plunger member 60 which is disposed within the barrel member 58. An abutment member 62 having a generally conical distal surface is affixed to the outer surface of the catheter body 44. First and second telescoping tube members 45, 49 are disposed within the interior of the plunger 60. The push wire 48 extends through the first telescoping tube member 45, and into the lumen of the second telescoping tube member 49, and is affixed thereto. The proximal end of the second telescoping tube member 49 is affixed in contact with the proximal end of the plunger 60, as shown in FIG. 5.

A longitudinal rigid abutment projection 70 extends into the interior of the barrel 58, and incorporates a generally conical depression 72 in the proximal end thereof. As the plunger 60 is forced in a distal direction, the generally conical distal surface of the abutment member 62 will abut against the generally conical depression of the abutment projection 70, and the generally cylindrical wall of the plunger 60 will enter the generally annular space 74 which surrounds the abutment projection 70. This allows the body of the plunger 60 to continue forward in the distal direction, while the abutment member 62, which is affixed to the outer surface of the catheter body 44, is unable to travel further in the distal direction due to its abutment against the abutment projection 70.

As will be described in greater detail below with respect to FIGS. 6a–6e, the initial movement of the plunger 60 in the forward direction, will cause the entire catheter body 44 to move forward such that the distal tubular member 40 will slidably advance through the sleeve 36, and will impinge against the radiused deflection surface 34 of the distal tip member 18. Further advancement of the plunger 60 will cause the distal tubular member 40 to be directed out of the side opening 32 of the distal tip member, by the radiused abutment surface 34, such that the distal portion of the distal tubular member 40 protrudes outwardly from the catheter body 12, in a direction substantially perpendicular to the longitudinal axis LA of the catheter body 12. Thereafter, continued pressure against the plunger 60 will cause the cylindrical body of the plunger 60 to continue forward within the annular space 74, thereby forcing the push wire 48 to advance through the catheter body 44. Such distal advancement of the push wire 48 propels the embolization coil 46 through the distal tubular member 40 and out of the distal end thereof.

After the embolization coil 46 has been expelled out of the distal end of the distal tubular member 40, the plunger 60 may be withdrawn in the proximal direction, thereby withdrawing the catheter body 44 and distal tubular member 40, fully into the second lumen 16 of the catheter body 12. The entire plunger 60, catheter body 44 and push wire 48 may be fully extracted and replaced by another replacement unit comprising another plunger 60, catheter body 44 and push wire 48, with yet another embolization coil 46 preloaded into the embolization catheter 44 as described hereabove and shown in FIGS. 3a and 3b. An ovoid window 76 (FIG. 5) is formed in the body of the barrel 58 to permit the operator to observe the advancement of the catheter body 44 and conical abutment member 62 as the plunger 60 is being depressed during the embolization coil deployment procedure. Referring to the distal end DE of the scope body 82, as seen in FIG. 2a, one or more illumination outlet ports 85 may also be provided to illuminate the visual field of the scope 80. Alternatively, the illumination outlet ports 85 and image receiving port 84 may be incorporated into a single port or lens surface whereby illuminating light is cast out of the distal end of the scope body 82 and an optical image is concurrently received therein. The illumination outlet ports 85 are connected to one or more bundles of illumination fibers which extend longitudinally through the scope body 82. Similarly, the optical image inlet port 84 comprises a lens or other communication means which is connected to one or more optical image transmitting fibers which extend longitudinally through the scope body 82. As seen in FIG. 1, the scope body 82 extends through the main body portion 52 of the proximal connector assembly 50, and is connected to a scope adjustment/control assembly 86. A handpiece portion 88 and proximal scope connector assembly 90 extend proximally from the scope adjustment/control assembly 86. The proximal connector assembly 90 incorporates a light source connector 92 whereby a light source may be connected to the illumination fiber(s) of the scope so as to pass illuminating light in the proximal direction through the scope body 82 and out of the illumination ports 82 on the distal end thereof Also, the proximal scope connector assembly 90 incorporates a camera connector 94 whereby a camera, eye piece, video monitor, video tape recorder and/or other video viewing devices may be connected to the optical image fibers of the scope 90 so as to electronically process and permit viewing of an optical image received through image receiving port 84.

Figures 2B, 2C:
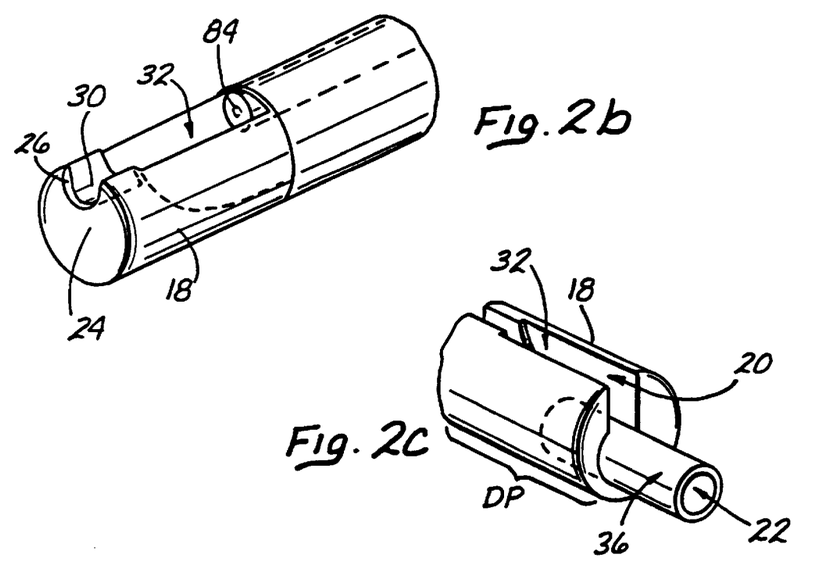
FIG. 2b is an enlarged perspective view of the device of FIG. 1, with the angioscopic component of the device in its proximally retracted position.
FIG. 2c is an enlarged, rear, perspective view of an insert member which forms a portion of the distal end of the device of FIG. 1.

As shown in the details of FIGS. 4 and 4a, the scope adjustment/control assembly 86 incorporates a fine adjustment mechanism 100 for precisely adjusting the longitudinal positioning of the scope 80 relative to the catheter body 12 of the device so as to eliminate any unwanted protrusion or malpositioning of the scope 80 due to variations in the tolerances or sizing of the scope 80 relative to the catheter body 12 of the device. Also, the scope adjustment/control assembly 86 incorporates a scope advancement/retraction mechanism 102 whereby the operator may volitionally move the scope 80 between its distally advanced position (FIGS. 2a, 3a) and its distally retracted position (FIGS. 2b, 3b).

The fine longitudinal adjustment mechanism 100 of the adjustment/control assembly 86 comprises a rotatable nut 106 disposed on the proximal end of the main body portion 52 of the Y-connector assembly 50. The rotatable nut 106 has an internally threaded passageway 108 extending longitudinally therethrough. The scope body 82 extends through the main body portion 52 of the proximal Y-connector assembly 50, and through the threaded inner passageway 108 of the rotatable nut 106. An externally threaded member 112 engages the internal threads of the rotatable nut 106. Rotation of the nut 106 in a first direction will cause the externally threaded member 112 and scope body 82 to advance in the distal direction, while opposite rotation of the nut 106 in the opposite direction will cause the externally threaded member 112 and scope body 82 to retract in the proximal direction. In this regard, rotatable nut 106 may be utilized to effect fine adjustment of the longitudinal positioning of the scope body 82 relative to the remainder of the device 10. Such fine adjustment may be accomplished to ensure that the distal end DE of the scope body 82 is properly positioned within the view port 26 prior to insertion of the device 10, thereby eliminating any improper scope positioning which could result from variability in the sizing or manufacturing tolerance of the scope devices 80 relative to the remainder of the device 10.

Further, with specific reference to FIGS. 4 and 4a, the scope advancement/retraction mechanism 102 comprises a generally cylindrical outer member 120 having a plurality of annular ribs 122 formed on the outer surface thereof to prevent slippage of the operators fingers as the annular member 120 is advanced and/or retracted. Engagement member 124 is firmly affixed to the scope body 82 and to the surrounding inner surface of the cylindrical member 120. An annular spring member 130 is positioned within an annular notch formed about the outer surface of engagement member 124, and a series of corresponding engagement notches or detents 131 are formed in the inner surface of the cylindrical member 120. Thus, cylindrical member 120, engagement member 124, scope body 82 and proximal scope connector assembly 90 may be concurrently moved back and forth, longitudinally, relative to the catheter body 12, proximal Y-connector assembly 50, fine adjustment mechanism 100, and handpiece 88. As such longitudinal movement is accomplished, the spring member 130 will engage the individual detents 131 to bias and hold the scope body 82 in selected longitudinal positions. In this regard, the operator may manually grasp and move the cylindrical member 120 to accomplish movement of the scope 80 between its distally advanced position (FIGS. 2a, 3a) wherein the illumination outlet ports 86 and imaging receiving port 84 of the scope 80 are positioned immediately adjacent, or within, the image receiving port 126 formed in the distal face 24 of the distal tip member 18, and the proximally retracted position (FIGS. 2b, 3b) wherein the illumination ports 86 and image receiving port 36 of the scope 80 are positioned immediately proximal to the side opening 32 formed in the distal tip member 18.

In this regard, when the scope 80 is in its distally advanced position (FIGS. 2a, 3a) the scope 80 may be utilized to visualize an area which is ahead of, and surrounding, the distal end DE of the catheter body 12, thereby facilitating advancement of the catheter body 12 through a blood vessel and location of any side branches of the blood vessel which are to be embolized and occluded. After the side branch of a vessel has been located, the scope 80 is withdrawn to its proximally retracted position (FIGS. 2b, 3b), whereby the scope 80 may be utilized to ensure that the radiused deflection surface 34 of the distal tip member 18 is positioned immediately adjacent the side branch into which the embolization coil 46 is to be ejected.

Thereafter, the scope 80 may continue to be utilized as the plunger 60 of the embolization catheter device 42 is depressed into the barrel 58, thereby causing the embolization catheter 44, including its distal tube member 40 to advance in the distal direction, being deflected by the radiused deflection surface 34 out of the side opening 32 and into the adjacently positioned side branch of the blood vessel. Thereafter, the scope 80 may continue to be utilized to view the passage of the embolization coil 46 through the distal tubular member 40 of the embolization catheter 44 and into the adjacent side branch. Thereafter, the scope 80 may continue to be utilized to view the retraction of the distal tube member 40 of the embolization catheter 44 into the second lumen 16 of the catheter body 12.

Thus, the longitudinal moveability of the scope 80 between its distally advanced position (FIGS. 2a, 3a) and its proximally retracted position (FIGS. 2b, 3b) permits the scope body 82 to be easily utilized for both the advancement and positioning of the catheter body 12 of the device 10, and the subsequent deployment of the embolization catheter device 42 into the intended side branch and ejection of the embolization coil 46 thereinto.

ii. The Preferred Method

FIGS. 6a–6e provide a step-by-step illustration of a preferred method of utilizing the device 10 to perform an endovascular side branch occlusion procedure under angioscopic guidance.

Generally, FIGS. 6a–6e show a blood vessel BV having a lumen $L_1$. A side branch SB having a side branch lumen $L_2$ emanates from the blood vessel BV, as shown. Also, for purposes of illustration, a venous valve VV is shown in a typical position within the lumen $L_1$ of blood vessel BV.

Prior to insertion of the device 10, the operator will manually ensure that cylindrical member 120 is in its fully distally advanced position and, thereafter, will manually rotate fine adjustment nut 106 to make certain that the distal end of the scope body 82 is properly positioned relative to the distal end surface 24 of the device 10. After such visual inspection and preparation of the device 10, the device is inserted and utilized as shown in FIGS. 6a–6e, and described herebelow.

Figure 6A:
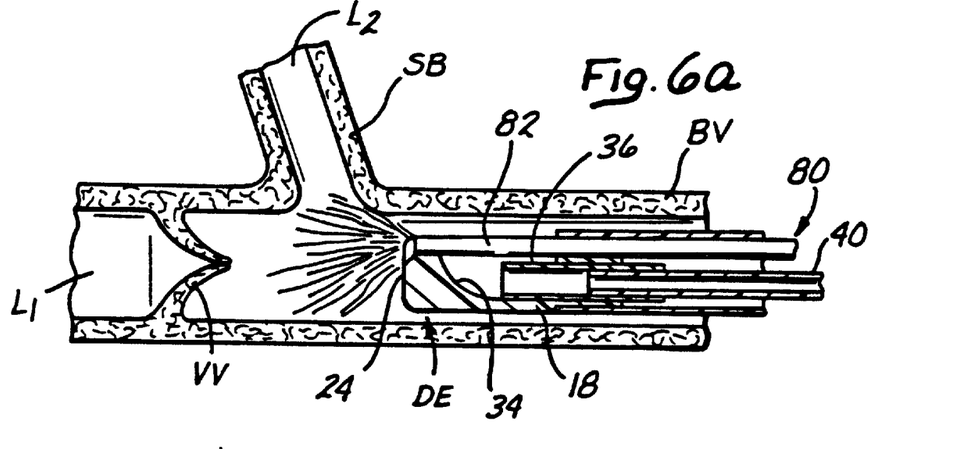
FIGS. 6a–6e are a step-wise showing of a method whereby the device of the present invention is utilized to effect endoluminal embolization of the side branch of a blood vessel, under angioscopic guidance and visualization.
Figure 6B:
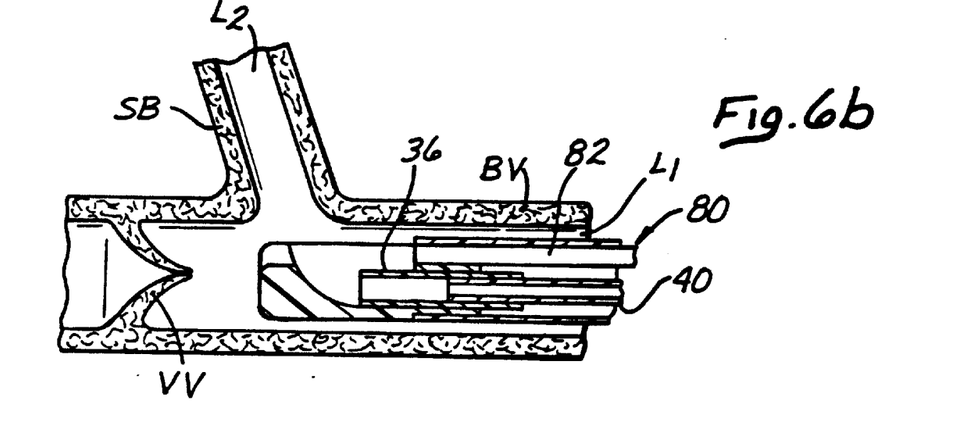

FIG. 6a shows an initial step in the method wherein the catheter body 12 of the device 10 has been inserted into the patient's vasculature and has been advanced transluminally into the segment of blood vessel BV wherein the side branch occlusion procedure is to be performed. The scope advancement/retraction mechanism 102 of the device 10 is manually advanced to its distal-most position, thereby causing the scope 80 to assume its distally advanced position wherein the distal end of the scope body 82 is positioned within the scope view port 26 formed in the distal face 24 of the distal tip member 18. When in such position the scope 80 provides a field of view which is ahead of the distal end DE of the device 10, as denoted by the shaded area in FIG. 6a. Thus, when so positioned, the scope 80 may be utilized to discern the presence and location of the side branch SB, and to facilitate the proper positioning of the side opening 32 of the device 10 next to the side branch SB of the blood vessel BV such that an embolization coil 46 may be volitionally passed into the side branch SB using the embolization device 42 carried within the catheter body 12. As shown in FIG. 6b, the scope advancement/retraction mechanism 102 is then moved to its proximal-most position, thereby retracting the endoscope 80 to its proximally retracted position. When in its proximally retracted position, the scope 80 provides a field of view which includes the ostium of the side branch SB, the side opening 32 of the device 10, and a portion of the radius deflection surface 34 which serves to guide the passage of the distal tubular member 40 of the embolization device 42 into the side branch SB. In this regard, the endoscope 80 is utilized to visually determine the proper positioning of the catheter body 12 relative to the side branch SB, such that the radiused deflection surface 34 is in alignment with the lumen $L_2$ of the side branch SB so as to deflect the distal tubular member 40 of the embolization device 42 into the lumen $L_2$ of the side branch SB.

Figure 6C:
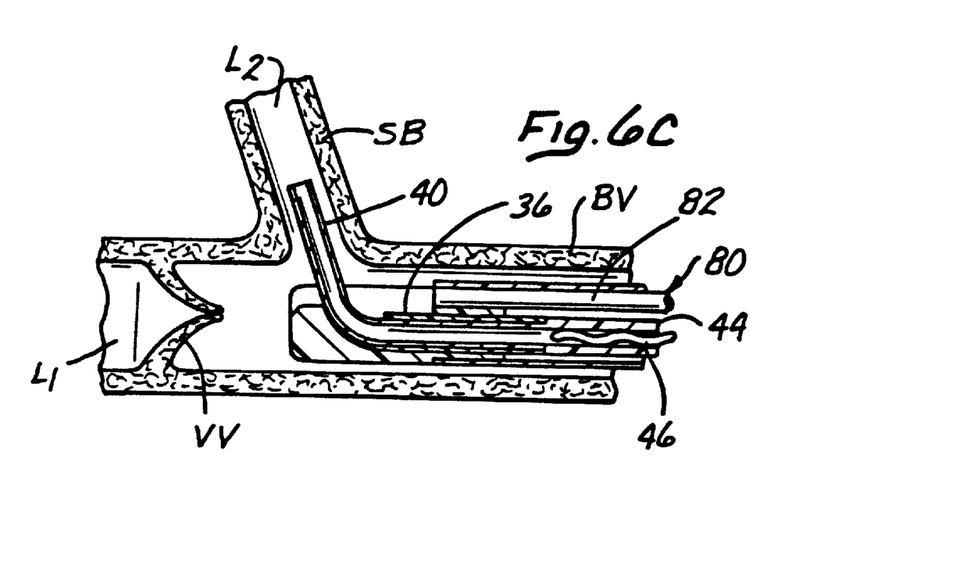

As shown in FIG. 6c, after the distal end DE of the catheter body 12 has been properly positioned, the plunger 60 is advanced into the barrel 58 of the embolization device 42, thereby causing the distal tubular member 40 to advance in the distal direction, and to be deflected by radiused deflection surface 34 into the lumen $L_2$ of the side branch SB.

Figure 6D:
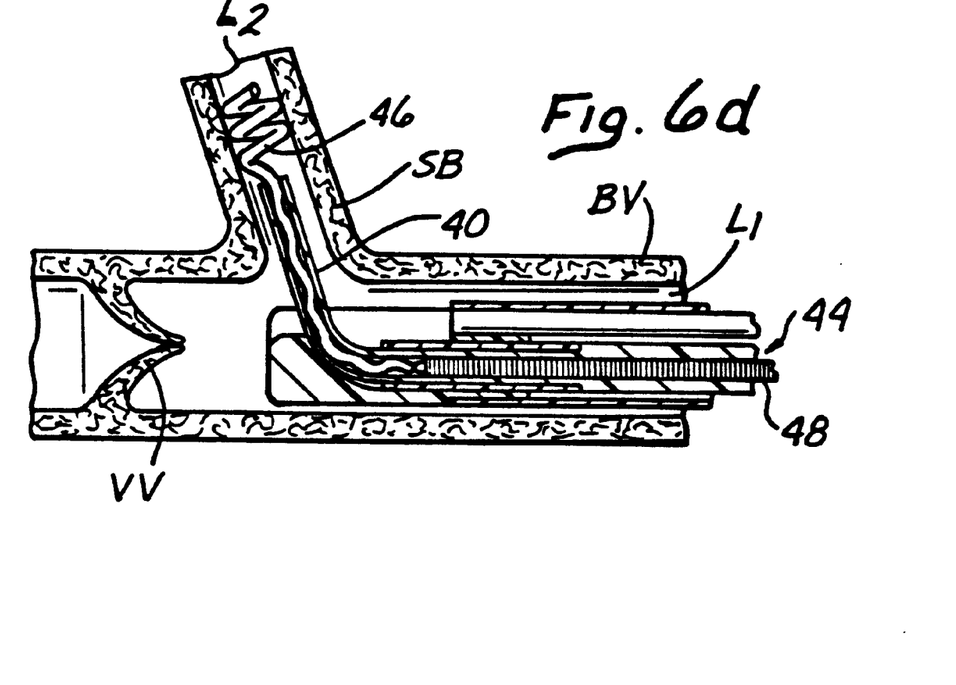

As shown in FIG. 6d, further advancement of the plunger 60 into the barrel 58 of the embolization device 42 causes the push wire 48 to advance in the distal direction, thereby pushing the embolization coil 46 through the lumen of the embolization catheter body 44, out of the distal end of the distal tubular member 40 and into the lumen $L_2$ of the side branch SB. As the embolization coil 46 passes out of the distal end of the distal tubular member 40, the embolization coil 46 resiliently assumes a tightly wound helical or other mass configuration, thereby forming an occlusion or blockage within the lumen $L_2$ of the side branch SB. After the embolization coil 46 has been fully deployed into the lumen $L_2$ of the side branch SB, the plunger 60 is withdrawn in the proximal direction, thereby retracting the embolization catheter body 44 in the proximal direction, and causing the distal tubular member 40 thereof to again become fully retracted into the second lumen 16 of the catheter body 12 of the device 10. Thereafter, the scope 80 may again be returned to its distally advanced position, and the catheter body 12 may be further advanced to the site of another side branch whereat the above-described side branch occlusion procedure is repeated.

Figure 6E:
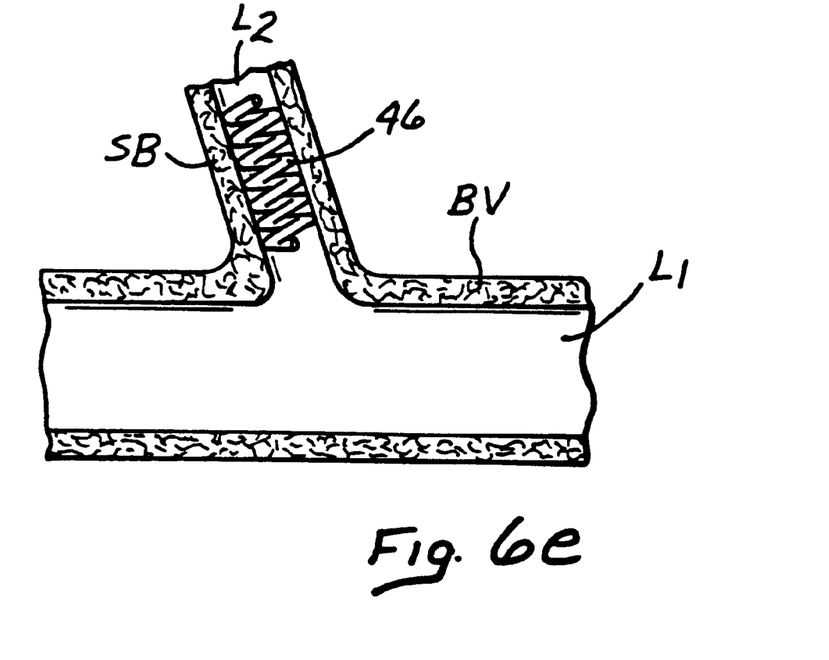

As shown in FIG. 6e, after all of the side branches SB have been occluded, the device 10 is removed from the blood vessel. The embolization coil 46 remains within the lumen $L_2$ of each side branch SB, as shown.

It will be appreciated that, when the scope 80 is in its distally advanced position, the angioscope 80 may be utilized to visually observe and guide the operation of a separate instrument located ahead of the distal end DE of the catheter body 12. For example, the scope 80 may be positioned in its distally advanced position and utilized to visually observe and guide the use of a separate endovascular valvulotome device for lysing the venous valves VV which are endogenous to the lumen LI of the blood vessel BV.

Any suitable type of valvulotome device may be utilized to cut the venous valves VV concurrently or in conjunction with the performance of the side branch blocking procedure of the present invention, under visualization by the scope 80 incorporated in the device of the present invention. One example of a valvulotome device which is usable in conjunction with the present invention is the device described in the U.S. Pat. No. 5,658,302 entitled METHOD AND DEVICE FOR ENDOLUMINAL DISRUPTION OF VENOUS VALVES (Wicherski et al), issued Aug. 19, 1997.

To facilitate angioscopic visualization of the device 10 of the present invention during its use, it will be appreciated that a clear liquid such as 0.9% NaCl or Ringer's lactate solution may be introduced into the lumen L of the blood vessel BV in a manner which displaces blood from the lumen L and provides an optically transparent environment for visualization by the scope 80. Such solution(s) may be infused through an introducer sheath which surrounds the device 10, particularly in cases where the device 10 has been inserted percutaneously. Alternatively, when a valvulotome device has been inserted in the retrograde or opposite direction, and is being used separately in conjunction with the device 10 of the present invention, the desired liquid may be infused through a liquid infusion lumen of the valvulotome device.

Alternatively, a separate irrigation catheter may be inserted into the vein and utilized to infuse the desired liquid into the lumen L of the blood vessel BV.

As another alternative, a separate fluid infusion lumen may be formed within the device 10 of the present invention, and may be coupled to an optional additional fluid infusion side arm 97 such that the desired liquid may be infused directly through the device 10 of the present invention, without the need for infusion of liquid through a separate introducer, catheter, valvulotome or other apparatus.

In summary, it is to be appreciated that the invention has been described herein with reference to certain presently preferred embodiments of the invention. Various changes, alterations, additions, and deletions may be made to the above-described preferred embodiments without departing from the intended spirit and scope of the present invention. Accordingly, it is intended that all such changes, alterations, deletions and modifications be encompassed within the scope of the following claims.

What is claimed is:

1. A method of blocking side branches which emanate from an anatomical passageway, the method comprising:

inserting an elongated, flexible device into an anatomical passageway, the device including a catheter body and first and second lumens extending longitudinally therethrough, the catheter body having a distal end near which is located a side opening communicating with the second lumen;

positioning an endoscope in a distally advanced position within the first lumen, the endoscope including a distal image receiving port that is positioned at the distal end of the catheter body in the distally advanced position of the endoscope, the endoscope occluding the side opening when in the distally advanced position;

advancing the catheter body, distal end first, through the anatomical passageway while observing the visual image provided by the endoscope;

stopping the advancement of the device when the visual image of the endoscope indicates that the distal end of the endoscope is adjacent a side branch emanating from the anatomical passageway;

retracting the endoscope to a proximally retracted position within the first lumen to expose the side opening to the anatomical side branch, the distal image receiving port being positioned proximal with respect to the side opening in the proximally retracted position of the endoscope to enable viewing of the anatomical side branch; and passing an embolization member from the second lumen out of the side opening and into the anatomical side branch.

2. The method of claim 1 further comprising:

returning the endoscope to its distally advanced position; and, further advancing the device, distal end first, while monitoring the visual image provided by the endoscope;

stopping the advancement of the device when the visual image of the endoscope indicates that the distal end of the endoscope is adjacent a second side branch emanating from the anatomical passageway; and repeating the steps of retracting and passing.

3. The method of claim 1 wherein the anatomical passageway is a vein having at least one side branch emanating therefrom and at least one venous valve located therein, and wherein the method further includes utilizing the endoscope while in the distally advanced position to endoscopically view the positioning and use of a separate valvulotome device to cut the venous valve.

4. The method of claim 1 further comprising, between the steps of retracting and passing:

adjusting the position of the device in the anatomical passageway to locate the side opening of the catheter body immediately adjacent the anatomical side branch.

5. The method of claim 4 further comprising:

providing a fine endoscope positioning mechanism and a coarse endoscope positioning mechanism, and wherein the step of retracting includes both coarse and fine positioning of the endoscope into an optimum viewing position with respect to the side opening.

6. The method of claim 1 further comprising:

providing an embolization catheter slidably disposed within the second lumen of the catheter body, the embolization member being slidably disposed within the embolization catheter, the device further including a deflection surface aligned with the second lumen; and wherein the step of passing includes distally advancing the embolization catheter with respect to the second lumen thus causing it to deflect against the deflection surface out of the side opening and into the anatomical side branch.

7. The method of claim 6 wherein the embolization member includes an embolization coil slidably disposed within the embolization catheter, the device further including a push member slidably disposed in the embolization catheter and behind the embolization coil; and wherein the step of passing includes distally advancing the push member with respect to the embolization catheter to contact and push the embolization coil from the embolization catheter and into the side branch.

8. The device of claim 7, wherein the push member and embolization catheter are coupled to slide together, the method further including preventing further advancement of the embolization catheter when the embolization catheter is deflected out of the side opening and into the anatomical side branch, while permitting the push member to continue to slide within the embolization catheter to deliver the embolization coil to the side branch.

9. A method of blocking side branches which emanate from an anatomical passageway, the method comprising:

inserting an elongated, flexible device into an anatomical passageway, the device including a catheter body and first and second lumens extending longitudinally therethrough, the catheter body having a distal end near which is located a side opening communicating with the second lumen and a deflection surface aligned with the second lumen;

advancing the catheter body, distal end first, through the anatomical passageway until the side opening is adjacent a side branch emanating from the anatomical passageway;

providing an endoscope within the first lumen, the endoscope including a distal image receiving port positioned proximal with respect to the side opening to enable viewing of the anatomical side branch;

providing an embolization catheter slidably disposed within the second lumen of the catheter body and an embolization member slidably disposed within the embolization catheter;

distally advancing the embolization catheter with respect to the second lumen thus causing it to deflect against the deflection surface out of the side opening and into the anatomical side branch; and pushing an embolization member from the embolization catheter and into the anatomical side branch.

10. The method of claim 9 wherein the step of advancing comprises:

positioning the endoscope in a distally advanced position within the first lumen so that the distal image receiving port is positioned at the distal end of the catheter body, the endoscope occluding the side opening when in the distally advanced position; and stopping the advancement of the device when the visual image of the endoscope indicates that the distal end of the endoscope is adjacent the side branch emanating from the anatomical passageway.

11. The method of claim 10 further comprising:

displacing the endoscope from the distally advanced position to the position within the first lumen proximal with respect to the side opening to expose the side opening to the anatomical side branch and enable viewing of the anatomical side branch by the distal image receiving port of the endoscope.

12. The method of claim 11 further comprising:

providing a fine endoscope positioning mechanism and a coarse endoscope positioning mechanism, and wherein the step of displacing the endoscope includes both coarse and fine positioning of the endoscope into an optimum viewing position with respect to the side opening.

13. The method of claim 11 further comprising:

proximally retracting the embolization catheter with respect to the second lumen thus causing it to withdraw from the anatomical side branch and side opening into the second lumen;

returning the endoscope to its distally advanced position thus occluding the side opening;

further advancing the device, distal end first, while monitoring the visual image provided by the endoscope;

stopping the advancement of the device when the visual image of the endoscope indicates that the distal end of the endoscope is adjacent a second side branch emanating from the anatomical passageway;

displacing the endoscope from the distally advanced position to the position within the first lumen proximal with respect to the side opening to expose the side opening to the anatomical side branch and enable viewing of the anatomical side branch by the distal image receiving port of the endoscope;

distally advancing the embolization catheter with respect to the second lumen again causing it to deflect against the deflection surface out of the side opening and into the second anatomical side branch;

providing a second embolization member slidably disposed within the embolization catheter;

pushing the second embolization member from the embolization catheter and into the second anatomical side branch.

14. The method of claim 10 wherein the anatomical passageway is a vein having at least one side branch emanating therefrom and at least one venous valve located therein, and wherein the method further includes utilizing the endoscope while in the distally advanced position to endoscopically view the positioning and use of a separate valvulotome device to cut the venous valve.

15. The method of claim 9 wherein the embolization member includes an embolization coil slidably disposed within the embolization catheter, the device further including a push member slidably disposed in the embolization catheter and behind the embolization coil; and wherein the step of pushing includes distally advancing the push member with respect to the embolization catheter to contact and push the embolization coil from the embolization catheter and into the side branch.

16. The device of claim 15, wherein the push member and embolization catheter are coupled to slide together, the method further including preventing further advancement of the embolization catheter when the embolization catheter is deflected out of the side opening and into the anatomical side branch, while permitting the push member to continue to slide within the embolization catheter to deliver the embolization coil to the side branch.

* * * * *